United States Patent
Sugiyama et al.

(10) Patent No.: US 9,950,985 B2
(45) Date of Patent: Apr. 24, 2018

(54) METHOD FOR PRODUCING COMPOSITION CONTAINING PURIFIED CHLOROGENIC ACIDS

(71) Applicant: KAO CORPORATION, Tokyo (JP)

(72) Inventors: Yukiteru Sugiyama, Narita (JP); Kenji Yamawaki, Narita (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/506,579

(22) PCT Filed: Aug. 18, 2015

(86) PCT No.: PCT/JP2015/073123
§ 371 (c)(1),
(2) Date: Feb. 24, 2017

(87) PCT Pub. No.: WO2016/031625
PCT Pub. Date: Mar. 3, 2016

(65) Prior Publication Data
US 2017/0305833 A1   Oct. 26, 2017

(30) Foreign Application Priority Data
Aug. 26, 2014 (JP) ................................ 2014-171326

(51) Int. Cl.
| | |
|---|---|
| *C07C 67/56* | (2006.01) |
| *C07C 69/732* | (2006.01) |
| *B01J 39/04* | (2017.01) |
| *A23L 33/105* | (2016.01) |
| *A23F 5/02* | (2006.01) |

(52) U.S. Cl.
CPC .............. *C07C 67/56* (2013.01); *A23F 5/02* (2013.01); *A23L 33/105* (2016.08); *B01J 39/04* (2013.01); *C07C 69/732* (2013.01); *A61K 2236/33* (2013.01)

(58) Field of Classification Search
None
See application file for complete search history.

(56) References Cited

U.S. PATENT DOCUMENTS

| | | | | |
|---|---|---|---|---|
| 4,481,223 A | * | 11/1984 | Hinman | A23F 5/223 426/422 |
| 2007/0160726 A1 | * | 7/2007 | Fujii | A23F 5/185 426/422 |
| 2013/0131165 A1 | * | 5/2013 | Sugiyama | C07C 67/56 514/533 |

FOREIGN PATENT DOCUMENTS

| | | |
|---|---|---|
| JP | 60-102143 A | 6/1985 |
| JP | 2001-78669 A | 3/2001 |
| JP | 2005-263632 A | 9/2005 |
| JP | 2006-174746 A | 7/2006 |
| JP | 2006-238773 * | 9/2006 |
| JP | 2006-238773 A | 9/2006 |
| JP | 2008-266144 A | 11/2008 |
| JP | 2012-31185 A | 2/2012 |
| JP | 2012-110322 A | 6/2012 |

OTHER PUBLICATIONS

Suarez-Quiroz, "Isolation of green coffee chlorogenic acids using activated carbon", Journal of Food Composition and Analysis, 2014, 33 (1), 55-58.*
International Search Report, issued in PCT/JP2015/073123, PCT/ISA/210, dated Nov. 17, 2015.
Suarez-Quiroa, "Isolation of green coffee chlorogenic acids using activated carbon", Journal of Food Composition and Analysis, Feb. 2014, 33 (1), 55-58.

* cited by examiner

*Primary Examiner* — Karl J Puttlitz
(74) *Attorney, Agent, or Firm* — Birch, Stewart, Kolasch & Birch, LLP

(57) ABSTRACT

Provided is a method of producing a purified chlorogenic acid-containing composition, including: a first step of dispersing or dissolving a raw material chlorogenic acid-containing composition in an aqueous solution of organic solvent; a second step of removing a precipitate from a dispersion or a solution obtained in the first step; and a third step of bringing a solution obtained in the second step into contact with activated carbon including activated carbon (A) having a pore volume of from 0.3 mL/g to 1.0 mL/g and activated carbon (B) having a pore volume larger than that of the activated carbon (A), in which a difference [(B)−(A)] in pore volume between the activated carbon (A) and the activated carbon (B) is from 0.1 mL/g to 1.5 mL/g.

16 Claims, No Drawings

METHOD FOR PRODUCING COMPOSITION CONTAINING PURIFIED CHLOROGENIC ACIDS

FIELD OF THE INVENTION

The present invention relates to a method of producing a purified chlorogenic acid-containing composition.

BACKGROUND OF THE INVENTION

As materials having physiological oactive functions, there have been proposed a variety of materials, and there are given polyphenols as those having physiological functions, such as an antioxidative effect, an antihypertensive effect, and a hepatic function-improving effect. A chlorogenic acid, which is one of the polyphenols, has been reported to have a high antihypertensive effect, and is expected to find a wide range of applications in supplements and food and drink.

Investigations have hence been carried out to make developments in elevating purity and stability of the chlorogenic acid. For example, it has been reported that, when an extract of green coffee beans or an extract of roasted coffee beans is treated so as to have a specific concentration of solids and then brought into contact with acid clay and/or activated clay, formation of precipitates immediately after production and formation of secondary precipitates during long-term storage can be suppressed (Patent Document 1). In addition, an acidic drink containing a chlorogenic acid has been investigated. As result, there is a report that: a chlorogenic acid-containing composition has a problem that the composition becomes turbid specifically in an acidic range when the composition is diluted to a concentration appropriate as a drink, while the composition does not become turbid when the composition contains a high concentration of the chlorogenic acid; and the turbidity that occurs specifically in an acidic range when the composition is diluted to a concentration appropriate as a drink can be suppressed by bringing a dispersion or a solution obtained by dispersing or dissolving a chlorogenic acid-containing composition in a mixed solvent of an organic solvent and water into contact with a specific adsorbent, removing the resulting precipitates, controlling the concentration of the chlorogenic acid and pH to specific ranges to further form precipitates, and then subjecting to solid-liquid separation (Patent Document 2).

[Patent Document 1] JP-A-2008-266144
[Patent Document 2] JP-A-2012-31165

SUMMARY OF THE INVENTION

The present invention provides a method of producing a purified chlorogenic acid-containing composition, comprising:

a first step of dispersing or dissolving a raw material chlorogenic acid-containing composition in an aqueous solution of organic solvent;

a second step of removing a precipitate from the dispersion or the solution obtained in the first step; and a third step of bringing the solution obtained in the second step into contact with activated carbon comprising activated carbon (A) having a pore volume of from 0.3 mL/g to 1.0 mL/g and activated carbon (B) having a pore volume larger than that of the activated carbon (A), wherein a difference [(B)−(A)] in pore volume between the activated carbon (A) and the activated carbon (B) is from 0.1 mL/g to 1.5 mL/g.

DETAILED DESCRIPTION OF THE INVENTION

In the above-mentioned related art, while investigations were carried out on suppression of precipitation after production and secondary precipitation during long-term storage, and on a suppression in turbidity caused specifically in an acidic region when a sample is diluted to a concentration appropriate as a drink, they did not focus attention on hue.

The present invention relates to a method of producing a purified chlorogenic acid-containing composition having a good hue even when the concentration of a chlorogenic acid is diluted to an optimum concentration as a drink to provide an acidic drink, having a suppressed turbidity after production, and having a reduced caffeine content without reducing the content of the chlorogenic acid.

The inventors of the present invention made various investigations, and as a result, found that a purified chlorogenic acid-containing composition having a good hue even when the concentration of a chlorogenic acid is diluted to an optimum concentration as a drink to provide an acidic drink, having a reduced turbidity after production, and having a reduced caffeine content can be produced without reducing the content of the chlorogenic acid by dispersing or dissolving a chlorogenic acid-containing composition in an aqueous solution of organic solvent to form a precipitate in the dispersion or the solution, removing the precipitate, and bringing the resultant into contact with two or more of activated carbon having specific properties.

The method of producing a purified chlorogenic acid-containing composition of the present invention is described below.

The method of producing a purified chlorogenic acid-containing composition of the present invention comprises a first step, a second step, and a third step. The steps are described below in detail.

(First Step)

The first step is a step of dispersing or dissolving a raw material chlorogenic acid-containing composition in an aqueous solution of organic solvent.

The raw material chlorogenic acid-containing composition is not particularly limited as long as the composition contains a chlorogenic acid, and for example, a plant extract containing the chlorogenic acid may be used. As the plant extract, there may be given, for example, those extracted from sunflower seeds, unripe apples, coffee beans, simon leaves, pinaceous cones, pinaceous seed hulls, sugarcane, nandina leaves, burdock, eggplant skins, Japanese plum fruit, colts foot, and vitaceous plants. An extraction method and extraction conditions are not particularly limited, and a known method and known conditions may be adopted. Of those, as the raw material chlorogenic acid-containing composition, an extract of coffee beans is preferred from the standpoint of the content of the chlorogenic acid or the like. In addition, coffee beans to be used for extraction are preferably green coffee beans or lightly roasted coffee beans, more preferably green coffee beans from the standpoint of the content of the chlorogenic acid or the like. The lightly roasted coffee beans have an L value of preferably 27 or more, more preferably 29 or more, more preferably 35 or more, even more preferably 45 or more, from the standpoint of the content of the chlorogenic acid, and of preferably less than 62, more preferably 60 or less, even more preferably 55 or less, from the viewpoint of taste and flavor. The L value of the lightly roasted coffee beans ranges preferably from 27 or more to less than 62, more preferably from 27 or more to 60 or less, more preferably from 29 or more to 55 or less, more preferably from 35 or more to 55 or less, even more preferably from 45 or more to 55 or less. The term "L value" as used herein refers to a value as determined by measuring the lightness of roasted coffee beans with a colorimeter under the assumption that black has an L value of 0 and white has an L value of 100.

The species of coffee tree may be any one of *Arabica, Robusta, Liberica*, and *Arabusta*. In addition, the producing region of the coffee beans is not particularly limited, and examples thereof include Brazil, Colombia, Tanzania, Mocha, Kilimanjaro, Mandheling, Blue Mountain, Guatemala, and Vietnam. The bean species and producing region of the coffee beans may be appropriately selected depending on preference, and two or more of coffee beans different in bean species or producing region may be used. In addition, two or more of coffee beans having different degree of roasting may be used. When coffee beans having different degree of roasting are used, coffee beans having L values outside the above-mentioned range may be used, but coffee beans are preferably appropriately combined so that the average of L values falls within the above-mentioned range. The average of L values is determined as a sum of values each determined by multiplying an L value of coffee beans by a content mass ratio of the coffee beans. The method for extraction from the coffee beans and extraction conditions thereof are not particularly limited, and a method disclosed in, for example, JP-A-58-138347, JP-A-59-51763, JP-A-62-111671, or JP-A-5-236918 may be adopted.

In addition, as the raw material chlorogenic acid-containing composition, a commercially available chlorogenic acid-containing preparation may be used, and an example thereof is Flavor Holder RC (manufactured by T. Hasegawa Co., Ltd.). The raw material chlorogenic acid-containing composition may be in any of various forms, such as a liquid, a slurry, a semisolid, and a solid.

The term "chlorogenic acid" as used herein is a collective term for monocaffeoylquinic acids including 3-caffeoylquinic acid, 4-caffeoylquinic acid, and 5-caffeoylquinic acid and monoferuloylquinic acids including 3-feruloylquinic acid, 4-feruloylquinic acid, and 5-feruloylquinic acid, and the content of the chlorogenic acid is defined based on the total amount of the above six chlorogenic acids.

The content of the chlorogenic acid in the solids of the raw material chlorogenic acid-containing composition is preferably 15 mass % or more, more preferably 20 mass % or more, even more preferably 25 mass % or more, and is preferably 70 mass % or less, more preferably 60 mass % or less, even more preferably 50 mass % or less. The content of the chlorogenic acid in the solids ranges preferably from 15 mass % to 70 mass %, more preferably from 20 mass % to 60 mass %, even more preferably from 25 mass % to 50 mass %. The term "solids" as used herein refers to a residue obtained by drying a sample in an electric thermostat dryer at 105° C. for 3 hours to remove volatile substances.

As an organic solvent in the aqueous solution of organic solvent to be used for dispersion or dissolution of the raw material chlorogenic acid-containing composition, there may be given, for example, an alcohol, such as ethanol or methanol, a ketone, such as acetone, and an ester, such as ethyl acetate. Of those, a hydrophilic organic solvent, such as an alcohol or a ketone, is preferred. In view of use in foods, an alcohol is more preferred, and ethanol is even more preferred.

The concentration of the organic solvent in the aqueous solution of organic solvent is preferably 10 mass % or more, more preferably 20 mass % or more, more preferably 30 mass % or more, even more preferably 40 mass % or more, from the viewpoints of improvement in stability of hue and a suppression in turbidity. It is preferably 95 mass % or less, more preferably 85 mass % or less, more preferably 75 mass % or less, even more preferably 70 mass % or less, from the standpoint of recovery rate of the chlorogenic acid. The concentration of the organic solvent ranges preferably from 10 mass % to 95 mass %, more preferably from 20 mass % to 85 mass %, more preferably from 30 mass % to 75 mass %, even more preferably from 40 mass % to 70 mass %.

As a method of adjusting the concentration of the aqueous solution of organic solvent, there may be given, for example, a method involving mixing the organic solvent with water so that the concentration of the organic solvent in the aqueous solution of organic solvent falls within the above-mentioned range, a method involving dissolving the raw material chlorogenic acid-containing composition in water and then adding the organic solvent so that the concentration of the organic solvent falls within the above-mentioned range, and a method involving suspending the raw material chlorogenic acid-containing composition in the organic solvent and then gradually adding water so that the concentration of the organic solvent falls within the above-mentioned range.

The usage amount of the aqueous solution of organic solvent is preferably 1 times by mass or more, more preferably 2 times by mass or more, even more preferably 3 times by mass or more, and is preferably 40 times by mass or less, more preferably 20 times by mass or less, even more preferably 10 times by mass or less, with respect to the solids of the raw material chlorogenic acid-containing composition, from the viewpoints of improvement in recovery rate of the chlorogenic acid and stability of hue, and a suppression in turbidity. The usage amount of the aqueous solution of organic solvent ranges preferably from 1 part by mass to 40 parts by mass, more preferably from 2 parts by mass to 20 parts by mass, even more preferably from 3 parts by mass to 10 parts by mass, with respect to the solids of the raw material chlorogenic acid-containing composition.

In this step, in mixing the raw material chlorogenic acid-containing composition with the aqueous solution of organic solvent to prepare a dispersion or a solution, at least one selected from the group consisting of acid clay, activated clay, and a filter aid may be mixed therewith.

The acid clay or the activated clay is not particularly limited as long as the acid clay or the activated clay contains, as general chemical components, $SiO_2$, $Al_2O_3$, $Fe_2O_3$, $CaO$, $MgO$, and the like, and has a mass ratio of $SiO_2/Al_2O_3$ of preferably from 3 to 12, more preferably from 4 to 9. In addition, the acid clay or the activated clay preferably has a composition containing 2 mass % to 5 mass % of $Fe_2O_3$, 0 mass % to 1.5 mass % of $CaO$, and 1 mass % to 7 mass % of $MgO$.

The activated clay is a product obtained by treating naturally occurring acid clay (montmorillonite-based clay) with a mineral acid, such as sulfuric acid, and is a compound having a porous structure with a large specific surface area and adsorption capability. When the acid clay is further treated with an acid, the specific surface area is modified, to thereby improve its decoloring capacity and change its physical properties.

The specific surface area of each of the acid clay and the activated clay varies depending on the degree of the acid treatment or the like, and is preferably from 50 $m^2/g$ to 350 $m^2/g$. In addition, the acid clay and the activated clay each have a pH (5% suspension, 20° C.) of preferably from 2.5 to 8, more preferably from 3.6 to 7. For example, a commercially available product such as MIZUKA ACE #600 (manufactured by Mizusawa Industrial Chemicals, Ltd.) may be used as the acid clay.

In this step, of the acid clay and the activated clay, the acid clay is preferably used.

The usage amount of each of the acid clay and the activated clay is preferably 10 parts by mass or more, more preferably 20 parts by mass or more, even more preferably 30 parts by mass or more, and is preferably 200 parts by mass or less, more preferably 150 parts by mass or less, even more preferably 100 parts by mass or less, with respect to 100 parts by mass of the solids of the raw material chlorogenic acid-containing composition, from the viewpoints of improvement in recovery rate of the chlorogenic acid and stability of hue, and a suppression in turbidity. The usage amount of each of the acid clay and the activated clay ranges preferably from 10 parts by mass to 200 parts by mass, more preferably from 20 parts by mass to 150 parts by mass, even more preferably from 30 parts by mass to 100 parts by mass, with respect to 100 parts by mass of the solids of the raw material chlorogenic acid-containing composition.

The filter aid is not particularly limited as long as the filter aid is usually used in the field of food industry, and examples thereof may include diatom earth, cellulose, and a combination thereof.

The usage amount of the filter aid is preferably 1 part by mass or more, more preferably 2 parts by mass or more, even more preferably 3 parts by mass or more, and is preferably 30 parts by mass or less, more preferably 25 parts by mass or less, even more preferably 20 parts by mass or less, with respect to 100 parts by mass of the solids of the raw material chlorogenic acid-containing composition, from the viewpoint of recovery rate of the chlorogenic acid. The usage amount of the filter aid ranges preferably from 1 part by mass to 30 parts by mass, more preferably from 2 parts by mass to 25 parts by mass, even more preferably from 3 parts by mass to 20 parts by mass, with respect to 100 parts by mass of the solids of the raw material chlorogenic acid-containing composition.

(Second Step)

The second step is a step of removing a precipitate from the dispersion or the solution obtained in the first step.

As a method of removing the precipitate, a method usually used in the field of food industry may be adopted, and examples thereof may include solid-liquid separation, such as paper filtration, centrifugal separation, and membrane filtration. One of solid-liquid separation may be carried out, or two or more thereof may be appropriately carried out in combination.

In the paper filtration, filter paper may be precoated with a filter aid. As the filter aid, those as mentioned above may be given. The usage amount of the filter aid may be the same as above. In addition, other filtration methods, such as pressure filtration and suction filtration, may be adopted.

As a centrifuge to be used for the centrifugal separation, there may be used a general instrument, such as a separating plate-shaped, cylinder-shaped, or decanter-shaped instrument. The temperature at the time of the centrifugal separation is preferably from 5° C. to 70° C., more preferably from 10° C. to 40° C., from the viewpoints of improvement in stability of hue and a suppression in turbidity. Further, the speed and time of rotation may be appropriately set. For example, in the case of the separating plate-shaped instrument, the rotation speed is preferably from 2,000 r/min to 10,000 r/min, more preferably from 2,500 r/min to 9,000 r/min, even more preferably from 3,000 r/min to 8,000 r/min, and the period of time is preferably from 0.2 minute to 75 minutes, more preferably from 0.5 minute to 60 minutes, even more preferably from 1 minute to 30 minutes.

As treatment conditions for the membrane filtration, the treatment may be carried out under general filtration conditions. The pore size of the membrane is preferably 0.1 μm or more, more preferably 0.15 μm or more, even more preferably 0.2 μm or more, from the viewpoints of improvement in stability of hue and a suppression in turbidity and from the viewpoints of recovery rate of the chlorogenic acid and efficiency of filtration, and is preferably 10 μm or less, more preferably 5 μm or less, even more preferably 2 μm or less, from the viewpoints of recovery rate of the chlorogenic acid and efficiency of filtration and from the viewpoints of improvement in stability of hue and a suppression in turbidity. The pore size of the membrane ranges preferably from 0.1 μm to 10 μm, more preferably from 0.15 μm to 5 μm, even more preferably from 0.2 μm to 2 μm. As a method of measuring the pore size of the membrane, there is given a general measurement method based on mercury intrusion porosimetry, a bubble point test, bacterial filtration porosimetry, or the like, and a value determined by the bubble point test is preferably used. As a material for the membrane to be used in the membrane filtration, there may be given, for example, a polymer membrane, a ceramic membrane, and a stainless steel membrane.

(Third Step)

The third step is a step of bringing the solution obtained in the second step into contact with activated carbon including activated carbon (A) having a pore volume of from 0.3 mL/g to 1.0 mL/g and activated carbon (B) having a pore volume larger than that of the activated carbon (A). The term "pore volume" as used herein refers to the total volume of the pores of activated carbon, and values of physical properties thereof are determined based on a nitrogen gas adsorption method.

The pore volume of the activated carbon may be measured by a general nitrogen gas adsorption method. As a measurement apparatus, there are given, for example, ASAP 2020 (manufactured by Micromeritics Instrument Corporation) and Autosorb-3B (manufactured by Quantachrome Instruments).

The activated carbon (A) has a pore volume of from 0.3 mL/g to 1.0 mL/g, and the pore volume is preferably 0.33 mL/g or more, more preferably 0.37 mL/g or more, more preferably 0.40 mL/g or more, even more preferably 0.43 mL/g or more, from the viewpoints of improvement in stability of hue and a suppression in turbidity, and is preferably 0.94 mL/g or less, more preferably 0.64 mL/g or less, more preferably 0.60 mL/g or less, even more preferably 0.55 mL/g or less, from the viewpoint of recovery rate of the chlorogenic acid. The pore volume of the activated carbon (A) ranges preferably from 0.33 mL/g to 0.94 mL/g, more preferably from 0.37 mL/g to 0.64 mL/g, more preferably from 0.40 mL/g to 0.60 mL/g, even more preferably from 0.43 mL/g to 0.55 mL/g.

The activated carbon (B) may have a pore volume within the above-mentioned range as long as the activated carbon (B) has a pore volume larger than that of the activated carbon (A). The pore volume of the activated carbon (B) is preferably 1.0 mL/g or more, more preferably 1.2 mL/g or more, more preferably 1.3 mL/g or more, even more preferably 1.4 mL/g or more, from the viewpoints of improvement in stability of hue and a suppression in turbidity, and is preferably 2.0 mL/g or less, more preferably 1.8 mL/g or less, more preferably 1.7 mL/g or less, even more preferably 1.6 mL/g or less, from the viewpoint of recovery rate of the chlorogenic acid. The pore volume of the activated carbon (B) ranges preferably from 1.0 mL/g to 2.0 mL/g, more preferably from 1.2 mL/g to 1.8 mL/g, more preferably from 1.3 mL/g to 1.7 mL/g, more preferably from 1.4 mL/g to 1.7 mL/g, even more preferably from 1.4 mL/g to 1.6 mL/g.

The difference [(B)−(A)] in pore volume between the activated carbon (A) and the activated carbon (B) is from 0.1 mL/g to 1.5 mL/g, and the difference is preferably 0.5 mL/g or more, more preferably 0.7 mL/g or more, even more preferably 0.9 mL/g or more, from the viewpoints of improvement in stability of hue and a suppression in turbidity, and is preferably 1.4 mL/g or less, more preferably 1.3 mL/g or less, more preferably 1.2 mL/g or less, even more preferably 1.1 mL/g or less, from the viewpoint of recovery rate of the chlorogenic acid. The difference [(B)−(A)] in pore volume ranges preferably from 0.5 mL/g to 1.5 mL/g, more preferably from 0.5 mL/g to 1.4 mL/g, more preferably from 0.7 mL/g to 1.3 mL/g, more preferably from 0.9 mL/g to 1.2 mL/g, even more preferably from 0.9 mL/g to 1.1 mL/g.

In addition, the ratio of the pore volume of the activated carbon (B) to the pore volume of the activated carbon (A), [(B)/(A)], is preferably 1.5 or more, more preferably 2.0 or more, more preferably 2.5 or more, even more preferably 3.1 or more, from the viewpoint of recovery rate of the chlorogenic acid, and is preferably 4.0 or less, more preferably 3.7 or less, more preferably 3.5 or less, even more preferably 3.3 or less, from the viewpoints of improvement in stability of hue and a suppression in turbidity. The ratio [(B)/(A)] ranges preferably from 1.5 to 4.0, more preferably from 2.0 to 3.7, more preferably from 2.5 to 3.5, even more preferably from 3.1 to 3.3, and may range from 1.5 to 3.5.

A raw material from which the activated carbon is derived is not particularly limited as long as the raw material is generally used in the food industry, and there may be given, for example, various organic raw materials, such as a wood material (for example, sawdust), coal, and palm shell. In addition, activated carbon having been activated by a gas, such as water vapor, or a chemical may be used. In addition, the activated carbon may be in a powdery, granular, or fibrous form, and the form may be appropriately selected.

In the present invention, activated carbon produced by carbonizing any of the above-mentioned organic raw materials and having desired pore volumes may be collected and used, and a commercially available product may also be used. Examples of the commercially available product may include granular Shirasagi WH2C SS, granular Shirasagi WH2C LSS, and granular Shirasagi KL (all of which are manufactured by Japan Enviro Chemicals Ltd.), Kuraray Coal GW, Kuraray Coal GWH, and Kuraray Coal GLC (all of which are manufactured by Kuraray Chemical Co., Ltd.), M20-SWC (manufactured by Calgon Mitsubishi Chemical Corporation), and Taiko SGP (manufactured by Futamura Chemical Co., Ltd.).

As a method for the contact with the activated carbon, for example, a batchwise method and a continuous method may be given. Of those, a continuous method involving continuously passing the solution through a column filled with activated carbon is preferred from the viewpoint of production efficiency. In the case of the continuous method, the space velocity (SV) with respect to the total volume of the activated carbon is preferably 0.05 $[h^{-1}]$ or more, more preferably 0.15 $[h^{-1}]$ or more, even more preferably 0.2 $[h^{-1}]$ or more, and is preferably 10 $[h^{-1}]$ or less, more preferably 5 $[h^{-1}]$ or less, even more preferably 1 $[h^{-1}]$ or less. The space velocity (SV) ranges preferably from 0.05 $[h^{-1}]$ to 10 $[h^{-1}]$, more preferably from 0.15 $[h^{-1}]$ to 5 $[h^{-1}]$, even more preferably from 0.2 $[h^{-1}]$ to 1 $[h^{-1}]$. In addition, the bed volume (BV) with respect to the total volume of the activated carbon is preferably 0.5 [v/v] or more, more preferably 1.0 [v/v] or more, even more preferably 1.5 [v/v] or more, and is preferably 20 [v/v] or less, more preferably 10 [v/v] or less, even more preferably 5.0 [v/v] or less. The bed volume (BV) ranges preferably from 0.5 [v/v] to 20 [v/v], more preferably from 1.0 [v/v] to 10 [v/v], even more preferably from 1.5 [v/v] to 5.0 [v/v].

In addition, the solution obtained in the second step may be brought into contact with a mixture of the activated carbon (A) and the activated carbon (B), or may be brought into contact with the activated carbon (A) and the activated carbon (B) separately. The solution is preferably brought into contact with the activated carbon (A) and the activated carbon (B) separately, and from the viewpoint of a suppression in turbidity, in particular, from the viewpoint of a suppression in turbidity at low temperature, the solution is more preferably brought into contact with the activated carbon (A) and then with the activated carbon (B).

Further, when the solution is brought into contact with the activated carbon (A) and the activated carbon (B) separately in a continuous manner, the activated carbon (A) and the activated carbon (B) may be filled in different columns or may be filled in one column by being laminated as respective layers of the activated carbon (A) and the activated carbon (B). In this case, the activated carbon (A) and the activated carbon (B) are preferably loaded on the upstream side and on the downstream side, respectively, with respect to the liquid flow direction.

The usage amount of the activated carbon (A) is preferably 0.2 time by mass or more, more preferably 0.4 time by mass or more, more preferably 0.5 time by mass or more, even more preferably 0.6 time by mass or more, with respect to the solids of the raw material chlorogenic acid-containing composition, from the viewpoints of improvement in stability of hue and a suppression in turbidity, and is preferably 2.0 times by mass or less, more preferably 1.7 times by mass or less, more preferably 1.5 times by mass or less, even more preferably 1.2 times by mass or less, from the viewpoint of recovery rate of the chlorogenic acid. The usage amount of the activated carbon (A) ranges preferably from 0.2 time by mass to 2.0 times by mass, more preferably from 0.4 time by mass to 2.0 times by mass, more preferably from 0.4 time by mass to 1.7 times by mass, more preferably from 0.5 time by mass to 1.5 times by mass, even more preferably from 0.6 time by mass to 1.2 times by mass, with respect to the solids of the raw material chlorogenic acid-containing composition.

The usage amount of the activated carbon (B) is preferably 0.1 time by mass or more, more preferably 0.15 time by mass or more, even more preferably 0.2 time by mass or more, with respect to the solids of the raw material chlorogenic acid-containing composition, from the viewpoints of improvement in stability of hue and a suppression in turbidity, and is preferably 0.8 time by mass or less, more preferably 0.6 time by mass or less, even more preferably 0.4 time by mass or less, from the viewpoint of recovery rate of the chlorogenic acid. The usage amount of the activated carbon (B) ranges preferably from 0.1 time by mass to 0.8 time by mass, more preferably from 0.15 time by mass to 0.6 time by mass, more preferably from 0.2 time by mass to 0.4 time by mass, with respect to the solids of the raw material chlorogenic acid-containing composition.

The mass ratio of the activated carbon (B) to the activated carbon (A), [(B)/(A)], is preferably 0.1 or more, more preferably 0.15 or more, more preferably 0.2 or more, even more preferably 0.25 or more, from the viewpoint, of recovery rate of the chlorogenic acid, and is preferably 2.5 or less, more preferably 1.0 or less, more preferably 0.7 or less, more preferably 0.6 or less, more preferably 0.5 or less, even more preferably 0.4 or less, from the viewpoints of improvement in stability of hue and a suppression in turbidity. The mass ratio [(B)/(A)] ranges preferably from 0.1 to 1.0, more preferably from 0.1 to 0.7, more preferably from 0.15 to 0.7, more preferably from 0.2 to 0.6, more preferably from 0.25 to 0.5, even more preferably from 0.25 to 0.4, and may range from 0.1 to 0.5.

The temperature in contact with the activated carbon is preferably 0° C. or more, more preferably 10° C. or more, even more preferably 15° C. or more, and is preferably 60° C. or less, more preferably 50° C. or less, even more preferably 40° C. or less. The contact temperature ranges preferably from 0° C. to 60° C., more preferably from 10° C. to 50° C., even more preferably from 15° C. to 40° C.

In addition, before contacting with the activated carbon, the concentration of the chlorogenic acid in the solution obtained in the second step may be adjusted. The concentration of the chlorogenic acid in the solution obtained in the second step is preferably 2.5 mass % or more, more preferably 3 mass % or more, more preferably 3.5 mass % or more, even more preferably 4 mass % or more, and is preferably 7 mass % or less, more preferably 6 mass % or less, more preferably 5.5 mass % or less, even more preferably 5 mass % or less, from the viewpoints of improvement in recovery rate of the chlorogenic acid and stability of hue, and a suppression in turbidity. The concentration of the chlorogenic acid ranges preferably from 2.5 mass % to 7 mass %, more preferably from 3 mass % to 6 mass %, more preferably from 3.5 mass % to 5.5 mass %, even more preferably from 4 mass % to 5 mass %. As a method of adjusting the concentration, there may be given, for example, a method involving adjusting the concentration of the chlorogenic acid to the above-mentioned range with one or two selected from the group consisting of water and an organic solvent at the time of solid-liquid separation, more specifically, during or after solid-liquid separation.

Further, in contacting with the activated carbon, or after contacting with the activated carbon, the pH (20° C.) of the solution before or after treatment with the activated carbon may be adjusted to 0 to 4 from the viewpoints of improvement in stability of hue and a suppression in turbidity in production of an acidic drink. From the viewpoints of improvement in stability of hue and a suppression in turbidity, the pH (20° C.) is preferably adjusted to any of values corresponding to from a strong acid to a weak acid, and is preferably 0.2 or more, more preferably 0.7 or more, more preferably 1.0 or more, even more preferably 1.5 or more, and is preferably 3.8 or less, more preferably 3.6 or less, more preferably 3.4 or less, even more preferably 3.2 or less. The pH ranges preferably from 0.2 to 3.8, more preferably from 0.7 to 3.6, more preferably from 1.0 to 3.4, even more preferably from 1.5 to 3.2.

As a method of adjusting the pH, there may be given, for example, a method involving adding an acid to the solution before or after treatment with activated carbon or a method involving bringing the solution before or after treatment with activated carbon into contact with a cation exchange resin. The pH adjustment may be carried out by one of method or by a combination of two or more of methods.

Examples of the acid to be used for the pH adjustment include: organic acids, such as citric acid, lactic acid, tartaric acid, succinic acid, malic acid, and ascorbic acid; inorganic acids, such as phosphoric acid and hydrochloric acid; and salts thereof.

In addition, an example of the cation exchange resin is a cation exchange resin having a sulfonic acid group, a carboxyl group, or a phosphoric acid group, and of those, a cation exchange resin having a sulfonic acid group is preferred. As a commercially available product thereof, there may be given, for example, Amberlite 200CT, Amberlite IR120B, Amberlite IR124, and Amberlite IR118 (all of which are available from Organo Corporation (supplier: Rohm and Haas Company, USA)), and DIAION SK1B, DIAION SK1BH, DIAION SK102, DIAION PK208, and DIAION PK212 (all of which are manufactured by Mitsubishi Chemical Corporation). The usage amount of the cation exchange resin is preferably from 0.1 mL/g to 10 mL/g, more preferably from 0.2 mL/g to 5 mL/g, even more preferably from 0.3 mL/g to 2 mL/g, with respect to the mass of the solids of the raw material chlorogenic acid-containing composition.

Of those, as a method of adjusting the pH, a method involving bringing the solution into contact with a cation exchange resin having been ion-exchanged into H-type is preferred.

As a method for the contact with the cation exchange resin, for example, a batchwise method and a continuous method may be given. Of those, a continuous method involving continuously passing the solution through a column filled with a cation exchange resin is preferred from the viewpoint of production efficiency. In the case of the continuous method, the solution may be treated with a column filled with the activated carbon and a column filled with the cation exchange resin, or may be treated with a column filled with both of the activated carbon and the cation exchange resin.

In addition, after contacting with the activated carbon, the solution having been treated with the activated carbon may be subjected to solid-liquid separation. As the solid-liquid separation, for example, paper filtration, centrifugal separation, and membrane filtration may be given. One of solid-liquid separation may be carried out, or two or more thereof may be carried out in combination. Specific operation methods are as described in the second step.

The purified chlorogenic acid-containing composition of the present invention can be obtained as described above, and the purified chlorogenic acid-containing composition may be in any of various forms such as a liquid, a slurry, a semisolid, or a solid.

The purified chlorogenic acid-containing composition may be a form of concentrated solution. As a concentration method, there may be given, for example, a normal-pressure concentration method involving vaporizing a solvent at normal pressure, a reduced-pressure concentration method involving vaporizing a solvent under reduced pressure, and a membrane concentration method involving removing a solvent by membrane separation. Of those, a reduced-pressure method is preferred from the standpoints of work efficiency and quality maintenance. The temperature at the time of concentration is preferably from 20° C. to 70° C., more preferably from 25° C. to 65° C., even more preferably from 30° C. to 60° C.

In addition, when the purified chlorogenic acid-containing composition is a solid as its product form, the composition may be pulverized by a known method, such as spray drying or freeze drying.

The purified chlorogenic acid-containing composition obtained by the production method of the present invention may have the following properties (i) to (v).

(i) The purified chlorogenic acid-containing composition may have a turbidity of preferably 200 NTU or less, more preferably 100 NTU or less, more preferably 40 NTU or less, even more preferably 20 NTU or less after production when the concentration of the chlorogenic acid is adjusted to 6 mass % (turbidity immediately after the concentration of the chlorogenic acid is adjusted to 6 mass %). The term "turbidity" as used herein refers to a value measured by a method to be described in Examples. In addition, the term "NTU" refers to a measurement unit of formazin turbidity making use of formazin turbidity standard.

(ii) The purified chlorogenic acid-containing composition may have a turbidity of preferably 500 NTU or less, more preferably 200 NTU or less, more preferably 100 NTU or less, more preferably 40 NTU or less, even more preferably 20 NTU or less after the concentration of the chlorogenic acid is adjusted to 6 mass % and the composition is stored at 5° C. for 12 hours.

(iii) The purified chlorogenic acid-containing composition may contain preferably 10 mass % to 80 mass %, more preferably 25 mass % to 75 mass %, even more preferably 40 mass % to 70 mass % of the chlorogenic acid with respect to the solids, from the viewpoint of taste and flavor.

(iv) The purified chlorogenic acid-containing composition may have a mass ratio (caffeine/chlorogenic acid) of caffeine to the chlorogenic acid of preferably 0.01 or less, more preferably 0.005 or less, even more preferably 0.002 or less, from the viewpoint of taste and flavor. The lower limit of the mass ratio of caffeine/chlorogenic acid is not particularly limited, and may be 0.

(v) The purified chlorogenic acid-containing composition may have a b value in the Lab color system of preferably from 0 to 2.0, more preferably from 0 to 1.0, more preferably from 0 to 0.8, even more preferably from 0 to 0.5 when the concentration of the chlorogenic acid is adjusted to 0.064 mass %.

The term "b value" as used herein refers to one of the coordinate values that represent hue and chroma when a color is represented by the Lab color system, and indicates the chroma of yellow color.

The present invention further discloses the following production method regarding the above-mentioned embodiment.

<1>

A method of producing a purified chlorogenic acid-containing composition, comprising:

a first step of dispersing or dissolving a raw material chlorogenic acid-containing composition in an aqueous solution of organic solvent;

a second step of removing a precipitate from the dispersion or the solution obtained in the first step; and a third step of bringing the solution obtained in the second step into contact with activated carbon comprising activated carbon (A) having a pore volume of from 0.3 mL/g to 1.0 mL/g and activated carbon (B) having a pore volume larger than that of the activated carbon (A), wherein a difference [(B)–(A)] in pore volume between the activated carbon (A) and the activated carbon (B) is from 0.1 mL/g to 1.5 mL/g.

<2>

The method of producing a purified chlorogenic acid-containing composition according to the above-mentioned item <1>, wherein the raw material chlorogenic acid-containing composition is preferably an extract of one or two or more of plants selected from the group consisting of sunflower seeds, unripe apples, coffee beans, simon leaves, pinaceous cones, pinaceous seed hulls, sugarcane, nandina leaves, burdock, eggplant skins, Japanese plum fruit, colts foot, and vitaceous plants, more preferably coffee beans, more preferably an extract of one or two kinds selected from the group consisting of green coffee beans and lightly roasted coffee beans, even more preferably an extract of green coffee beans.

<3>

The method of producing a purified chlorogenic acid-containing composition according to the above-mentioned item <2>, wherein the lightly roasted coffee beans have an L value of preferably 27 or more, more preferably 29 or more, more preferably 35 or more, even more preferably 45 or more, and of preferably less than 62, more preferably 60 or less, even more preferably 55 or less.

<4>

The method of producing a purified chlorogenic acid-containing composition according to the above-mentioned item <2> or <3>, wherein the lightly roasted coffee beans have an L value of preferably 27 or more and less than 62, more preferably 27 or more and 60 or less, more preferably 29 or more and 55 or less, more preferably 35 or more and 55 or less, even more preferably 35 or more and 55 or less.

<5>

The method of producing a purified chlorogenic acid-containing composition according to any one of the above-mentioned items <1> to <4>, wherein the content of a chlorogenic acid in the solids of the raw material chlorogenic acid-containing composition is preferably 15 mass % or more, more preferably 20 mass % or more, even more preferably 25 mass % or more, and is preferably 70 mass % or less, more preferably 60 mass % or less, even more preferably 50 mass % or less.

<6>

The method of producing a purified chlorogenic acid-containing composition according to any one of the above-mentioned items <1> to <5>, wherein the content of the chlorogenic acid in the solids of the raw material chlorogenic acid-containing composition is preferably from 15 mass % to 70 mass %, more preferably from 20 mass % to 60 mass %, even more preferably from 25 mass % to 50 mass %.

<7>

The method of producing a purified chlorogenic acid-containing composition according to any one of the above-mentioned items <1> to <6>, wherein an organic solvent in the aqueous solution of organic solvent is preferably one or two or more selected from the group consisting of an alcohol, a ketone, and an ester, more preferably one or two or more selected from the group consisting of an alcohol and a ketone, more preferably an alcohol, even more preferably ethanol.

<8>

The method of producing a purified chlorogenic acid-containing composition according to any one of the above-mentioned items <1> to <7>, wherein the concentration of the organic solvent in the aqueous solution of organic solvent is preferably 10 mass % or more, more preferably 20 mass % or more, more preferably 30 mass % or more, even more preferably 40 mass % or more, and is preferably 95 mass % or less, more preferably 85 mass % or less, even more preferably 75 mass % or less.

<9>

The method of producing a purified chlorogenic acid-containing composition according to any one of the above-mentioned items <1> to <8>, wherein the concentration of the organic solvent in the aqueous solution of organic solvent is preferably from 10 mass % to 95 mass %, more preferably from 20 mass % to 85 mass %, more preferably from 30 mass % to 75 mass %, even more preferably from 40 mass % to 70 mass %.

<10>

The method of producing a purified chlorogenic acid-containing composition according to any one of the above-mentioned items <1> to <9>, wherein the usage amount of the aqueous solution of organic solvent is preferably 1 time by mass or more, more preferably 2 times by mass or more, even more preferably 3 times by mass or more, and is preferably 40 times by mass or less, more preferably 20 times by mass or less, even more preferably 10 times by mass or less, with respect to the solids of the raw material chlorogenic acid-containing composition.

<11>

The method of producing a purified chlorogenic acid-containing composition according to any one of the above-mentioned items <1> to <10>, wherein the usage amount of the aqueous solution of organic solvent is preferably from 1 part by mass to 40 parts by mass, more preferably from 2 parts by mass to 20 parts by mass, even more preferably from 3 parts by mass to 10 parts by mass, with respect to the solids of the raw material chlorogenic acid-containing composition.

<12>

The method of producing a purified chlorogenic acid-containing composition according to any one of the above-mentioned items <1> to <11>, wherein in the first step, one or two or more selected from the group consisting of acid clay, activated clay, and a filter aid is preferably added.

<13>

The method of producing a purified chlorogenic acid-containing composition according to the above-mentioned item <12>, wherein the usage amount of the acid clay and the activated clay is preferably 10 parts by mass or more, more preferably 20 parts by mass or more, even more preferably 30 parts by mass or more, and is preferably 200 parts by mass or less, more preferably 150 parts by mass or less, even more preferably 100 parts by mass or less, with respect to 100 parts by mass of the solids of the raw material chlorogenic acid-containing composition.

<14>

The method of producing a purified chlorogenic acid-containing composition according to the above-mentioned item <12> or <13>, wherein the usage amount of the acid clay and the activated clay is preferably from 10 parts by mass to 200 parts by mass, more preferably from 20 parts by mass to 150 parts by mass, even more preferably from 30 parts by mass to 100 parts by mass, with respect to 100 parts by mass of the solids of the raw material chlorogenic acid-containing composition.

<15>

The method of producing a purified chlorogenic acid-containing composition according to any one of the above-mentioned items <1> to <14>, wherein a method of removing a precipitate according to the second step is preferably one or two or more of solid-liquid separation selected from the group consisting of paper filtration, centrifugal separation, and membrane filtration.

<16>

The method of producing a purified chlorogenic acid-containing composition according to the above-mentioned item <15>, comprising, when the method of removing a precipitate according to the second step is the paper filtration, preferably precoating filter paper with a filter aid.

<17>

The method of producing a purified chlorogenic acid-containing composition according to the above-mentioned item <12> or <16>, wherein the filter aid is preferably diatom earth, cellulose, or a combination thereof.

<18>

The method of producing a purified chlorogenic acid-containing composition according to the above-mentioned item <12>, <16>, or <17>, wherein the usage amount of the filter aid is preferably 1 part by mass or more, more preferably 2 parts by mass or more, even more preferably 3 parts by mass or more, and is preferably 30 parts by mass or less, more preferably 25 parts by mass or less, even more preferably 20 parts by mass or less, with respect to 100 parts by mass of the solids of the raw material chlorogenic acid-containing composition.

<19>

The method of producing a purified chlorogenic acid-containing composition according to any one of the above-mentioned items <12> and <16> to <18>, wherein the usage amount of the filter aid is preferably from 1 part by mass to 30 parts by mass, more preferably from 2 parts by mass to 25 parts by mass, even more preferably from 3 parts by mass to 20 parts by mass, with respect to 100 parts by mass of the solids of the raw material chlorogenic acid-containing composition.

<20>

The method of producing a purified chlorogenic acid-containing composition according to the above-mentioned item <15>, wherein, when the method of removing a precipitate according to the second step is the centrifugal separation, the centrifugal separation is carried out at a temperature of preferably from 5° C. to 70° C., more preferably from 10° C. to 40° C.

<21>

The method of producing a purified chlorogenic acid-containing composition according to the above-mentioned item <15> or <20>, wherein, when the method of removing a precipitate according to the second step is the centrifugal separation, the centrifugal separation is carried out at a rotation speed of preferably from 2,000 r/min to 10,000 r/min, more preferably from 2,500 r/min to 9,000 r/min, even more preferably from 3,000 r/min to 8,000 r/min, for a period of time of preferably from 0.2 minute to 75 minutes, more preferably from 0.5 minute to 60 minutes, even more preferably from 1 minute to 30 minutes.

<22>

The method of producing a purified chlorogenic acid-containing composition according to the above-mentioned item <15>, wherein, when the method of removing a precipitate according to the second step is the membrane filtration, the pore size of the membrane is preferably 0.1 µm or more, more preferably 0.15 µm or more, even more preferably 0.2 µm or more, and is preferably 10 µm or less, more preferably 5 µm or less, even more preferably 2 µm or less.

<23>

The method of producing a purified chlorogenic acid-containing composition according to the above-mentioned item <15> or <22>, wherein, when the method of removing a precipitate according to the second step is the membrane filtration, the pore size of the membrane is preferably from 0.1 µm to 10 µm, more preferably from 0.15 µm to 5 µm, even more preferably from 0.2 µm to 2 µm.

<24>

The method of producing a purified chlorogenic acid-containing composition according to the above-mentioned item <15>, <22>, or <23>, wherein a material for the membrane to be used in the membrane filtration is preferably a polymer membrane, a ceramic membrane, or a stainless steel membrane.

<25>

The method of producing a purified chlorogenic acid-containing composition according to any one of the above-mentioned items <1> to <24>, wherein the pore volume of the activated carbon to be used in the third step is preferably determined based on a nitrogen gas adsorption method.

<26>

The method of producing a purified chlorogenic acid-containing composition according to any one of the above-mentioned items <1> to <25>, wherein the activated carbon (A) has a pore volume of preferably 0.33 mL/g or more, more preferably 0.37 mL/g or more, more preferably 0.40 mL/g or more, even more preferably 0.43 mL/g or more, and of preferably 0.94 mL/g or less, more preferably 0.64 mL/g or less, more preferably 0.60 mL/g or less, even more preferably 0.55 mL/g or less.

<27>

The method of producing a purified chlorogenic acid-containing composition according to any one of the above-mentioned items <1> to <26>, wherein the activated carbon (A) has a pore volume of preferably from 0.33 mL/g to 0.94 mL/g, more preferably from 0.37 mL/g to 0.64 mL/g, more preferably from 0.40 mL/g to 0.60 mL/g, even more preferably from 0.43 mL/g to 0.55 mL/g.

<28>

The method of producing a purified chlorogenic acid-containing composition according to any one of the above-mentioned items <1> to <27>, wherein the activated carbon (B) has a pore volume of preferably 1.0 mL/g or more, more preferably 1.2 mL/g or more, more preferably 1.3 mL/g or more, even more preferably 1.4 mL/g or more, and of preferably 2.0 mL/g or less, more preferably 1.8 mL/g or less, more preferably 1.7 mL/g or less, even more preferably 1.6 mL/g or less.

<29>

The method of producing a purified chlorogenic acid-containing composition according to any one of the above-mentioned items <1> to <28>, wherein the activated carbon (B) has a pore volume of preferably from 1.0 mL/g to 2.0 mL/g, more preferably from 1.2 mL/g to 1.8 mL/g, more preferably from 1.3 mL/g to 1.7 mL/g, more preferably from 1.4 mL/g to 1.7 mL/g, even more preferably from 1.4 mL/g to 1.6 mL/g.

<30>

The method of producing a purified chlorogenic acid-containing composition according to any one of the above-mentioned items <1> to <29>, wherein a difference [(B)–(A)] between the pore volumes is preferably 0.5 mL/g or more, more preferably 0.7 mL/g or more, even more preferably 0.9 mL/g or more, and is preferably 1.4 mL/g or less, more preferably 1.3 mL/g or less, more preferably 1.2 mL/g or less, even more preferably 1.1 mL/g or less.

<31>

The method of producing a purified chlorogenic acid-containing composition according to any one of the above-mentioned items <1> to <30>, wherein the difference [(B)–(A)] between the pore volumes is preferably from 0.5 mL/g to 1.5 mL/g, more preferably from 0.5 mL/g to 1.4 mL/g, more preferably from 0.7 mL/g to 1.3 mL/g, more preferably from 0.9 mL/g to 1.2 mL/g, even more preferably from 0.9 mL/g to 1.1 mL/g.

<32>

The method of producing a purified chlorogenic acid-containing composition according to any one of the above-mentioned items <1> to <31>, wherein the ratio of the pore volume of the activated carbon (B) to the pore volume of the activated carbon (A), [(B)/(A)], is preferably 1.5 or more, more preferably 2.0 or more, more preferably 2.5 or more, even more preferably 3.1 or more, and is preferably 4.0 or less, more preferably 3.7 or less, more preferably 3.5 or less, even more preferably 3.3 or less.

<33>

The method of producing a purified chlorogenic acid-containing composition according to any one of the above-mentioned items <1> to <32>, wherein the ratio of the pore volume of the activated carbon (B) to the pore volume of the activated carbon (A), [(B)/(A)], is preferably from 1.5 to 4.0, more preferably from 2.0 to 3.7, more preferably from 2.5 to 3.5, even more preferably from 3.1 to 3.3, and may be from 1.5 to 3.5.

<34>

The method of producing a purified chlorogenic acid-containing composition according to any one of the above-mentioned items <1> to <33>, wherein a raw material from which the activated carbon to be used in the third step is derived is preferably at least one selected from the group consisting of a wood material (for example, sawdust), coal, and palm shell.

<35>

The method of producing a purified chlorogenic acid-containing composition according to any one of the above-mentioned items <1> to <34>, wherein the activated carbon to be used in the third step is preferably activated carbon having been activated, more preferably activated carbon having been activated by a gas or activated carbon having been activated by a chemical.

<36>

The method of producing a purified chlorogenic acid-containing composition according to any one of the above-mentioned items <1> to <35>, wherein the activated carbon to be used in the third step is preferably in a powder, granular, or fibrous form.

<37>

The method of producing a purified chlorogenic acid-containing composition according to any one of the above-mentioned items <1> to <36>, wherein a method for the contact with the activated carbon according to the third step is preferably a batchwise method or a continuous method, more preferably a continuous method involving continuously passing the solution through a column filled with the activated carbon.

<38>

The method of producing a purified chlorogenic acid-containing composition according to the above-mentioned item <37>, wherein, when the method for the contact with the activated carbon according to the third step is the continuous method, the space velocity (SV) with respect to the total volume of the activated carbon is preferably 0.05 $[h^{-1}]$ or more, more preferably 0.15 $[h^{-1}]$ or more, even more preferably 0.2 $[h^{-1}]$ or more, and is preferably 10 $[h^{-1}]$ or less, more preferably 5 $[h^{-1}]$ or less, even more preferably 1 $[h^{-1}]$ or less.

<39>

The method of producing a purified chlorogenic acid-containing composition according to the above-mentioned item <37> or <38>, wherein, when the method for the contact with the activated carbon according to the third step is the continuous method, the space velocity (SV) with respect to the total volume of the activated carbon is preferably from 0.05 [h$^{-1}$] to 10 [h$^{-1}$], more preferably from 0.15 [h$^{-1}$] to 5 [h$^{-1}$], even more preferably from 0.2 [h$^{-1}$] to 1 [h$^{-1}$].

<40>

The method of producing a purified chlorogenic acid-containing composition according to any one of the above-mentioned items <37> to <39>, wherein, when the method for the contact with the activated carbon according to the third step is the continuous method, the bed volume (BV) with respect to the total volume of the activated carbon is preferably 0.5 [v/v] or more, more preferably 1.0 [v/v] or more, even more preferably 1.5 [v/v] or more, and is preferably 20 [v/v] or less, more preferably 10 [v/v] or less, even more preferably 5.0 [v/v] or less.

<41>

The method of producing a purified chlorogenic acid-containing composition according to any one of the above-mentioned items <37> to <40>, wherein, when the method for the contact with the activated carbon according to the third step is the continuous method, the bed volume (BV) with respect to the total volume of the activated carbon is preferably from 0.5 [v/v] to 20 [v/v], more preferably from 1.0 [v/v] to 10 [v/v], even more preferably from 1.5 [v/v] to 5.0 [v/v].

<42>

The method of producing a purified chlorogenic acid-containing composition according to any one of the above-mentioned items <1> to <41>, wherein the in third step, the solution obtained in the second step preferably is brought into contact with the activated carbon (A) and the activated carbon (B) separately, more preferably the solution obtained in the second step is brought into contact with the activated carbon (A) and then with the activated carbon (B).

<43>

The method of producing a purified chlorogenic acid-containing composition according to any one of the above-mentioned items <1> to <42>, wherein in the third step, preferably, the activated carbon (A) is loaded on the upstream side and the activated carbon (B) is loaded on the downstream side, with respect to the liquid flow direction of the solution obtained in the second step.

<44>

The method of producing a purified chlorogenic acid-containing composition according to any one of the above-mentioned items <1> to <43>, wherein the usage amount of the activated carbon (A) according to the third step is preferably 0.2 time by mass or more, more preferably 0.4 time by mass or more, more preferably 0.5 time by mass or more, even more preferably 0.6 time by mass or more, and is preferably 2.0 times by mass or less, more preferably 1.7 times by mass or less, more preferably 1.5 times by mass or less, even more preferably 1.2 times by mass or less, with respect to the solids of the raw material chlorogenic acid-containing composition.

<45>

The method of producing a purified chlorogenic acid-containing composition according to any one of the above-mentioned items <1> to <44>, wherein the usage amount of the activated carbon (A) according to the third step is preferably from 0.2 time by mass to 2.0 times by mass, more preferably from 0.4 time by mass to 2.0 times by mass, more preferably from 0.4 time by mass to 1.7 times by mass, more preferably from 0.5 time by mass to 1.5 times by mass, even more preferably from 0.6 time by mass to 1.2 times by mass, with respect to the solids of the raw material chlorogenic acid-containing composition.

<46>

The method of producing a purified chlorogenic acid-containing composition according to any one of the above-mentioned items <1> to <45>, wherein the usage amount of the activated carbon (B) according to the third step is preferably 0.1 time by mass or more, more preferably 0.15 time by mass or more, even more preferably 0.2 time by mass or more, and is preferably 0.8 time by mass or less, more preferably 0.6 time by mass or less, even more preferably 0.4 time by mass or less, with respect to the solids of the raw material chlorogenic acid-containing composition.

<47>

The method of producing a purified chlorogenic acid-containing composition according to any one of the above-mentioned items <1> to <46>, wherein the usage amount of the activated carbon (B) according to the third step is preferably from 0.1 time by mass to 0.8 time by mass, more preferably from 0.15 time by mass to 0.6 time by mass, more preferably from 0.2 time by mass to 0.4 time by mass, with respect to the solids of the raw material chlorogenic acid-containing composition.

<48>

The method of producing a purified chlorogenic acid-containing composition according to any one of the above-mentioned items <1> to <47>, wherein the mass ratio of the activated carbon (B) to the activated carbon (A), [(B)/(A)], according to the third step is preferably 0.1 or more, more preferably 0.15 or more, more preferably 0.2 or more, even more preferably 0.25 or more, and is preferably 1.0 or less, more preferably 0.7 or less, more preferably 0.6 or less, more preferably 0.5 or less, even more preferably 0.4 or less.

<49>

The method of producing a purified chlorogenic acid-containing composition according to any one of the above-mentioned items <1> to <48>, wherein the mass ratio of the activated carbon (B) to the activated carbon (A), [(B)/(A)], according to the third step is preferably from 0.1 to 1.0, more preferably from 0.1 to 0.7, more preferably from 0.15 to 0.7, more preferably from 0.2 to 0.6, more preferably from 0.25 to 0.5, even more preferably from 0.25 to 0.4, and may be from 0.1 to 0.5.

<50>

The method of producing a purified chlorogenic acid-containing composition according to any one of the above-mentioned items <1> to <49>, wherein the temperature in contact with the activated carbon according to the third step is preferably 0° C. or more, more preferably 10° C. or more, even more preferably 15° C. or more, and is preferably 60° C. or less, more preferably 50° C. or less, even more preferably 40° C. or less.

<51>

The method of producing a purified chlorogenic acid-containing composition according to any one of the above-mentioned items <1> to <50>, wherein the temperature in contact with the activated carbon according to the third step is preferably from 0° C. to 60° C., more preferably from 10° C. to 50° C., even more preferably from 15° C. to 40° C.

<52>

The method of producing a purified chlorogenic acid-containing composition according to any one of the above-mentioned items <1> to <51>, further comprising, before the third step, a step of adjusting the concentration of the chlorogenic acid in the solution obtained in the second step.

<53>

The method of producing a purified chlorogenic acid-containing composition according to the above-mentioned item <52>, wherein the concentration of the chlorogenic acid in the solution obtained in the second step is adjusted to preferably 2.5 mass % or more, more preferably 3 mass % or more, more preferably 3.5 mass % or more, even more preferably 4 mass % or more, and to preferably 7 mass % or less, more preferably 6 mass % or less, more preferably 5.5 mass % or less, even more preferably 5 mass % or less.

<54>

The method of producing a purified chlorogenic acid-containing composition according to the above-mentioned item <52> or <53>, wherein the concentration of the chlorogenic acid in the solution obtained in the second step is adjusted to preferably from 2.5 mass % to 7 mass %, more preferably from 3 mass % to 6 mass %, more preferably from 3.5 mass % to 5.5 mass %, even more preferably from 4 mass % to 5 mass %.

<55>

The method of producing a purified chlorogenic acid-containing composition according to any one of the above-mentioned items <1> to <54>, further comprising, after the second step and before the third step, or after the third step, a step of adjusting the pH (20° C.) of the solution before treatment with the activated carbon or after treatment with the activated carbon to preferably 0 or more, more preferably 0.2 or more, more preferably 0.7 or more, more preferably 1.0 or more, even more preferably 1.5 or more, and to preferably 4 or less, more preferably 3.8 or less, more preferably 3.6 or less, more preferably 3.4 or less, even more preferably 3.2 or less.

<56>

The method of producing a purified chlorogenic acid-containing composition according to any one of the above-mentioned items <1> to <55>, further comprising, after the second step and before the third step, or after the third step, a step of adjusting the pH (20° C.) of the solution before treatment with the activated carbon or after treatment with the activated carbon to preferably from 0.2 to 3.8, more preferably from 0.7 to 3.6, more preferably from 1.0 to 3.4, even more preferably from 1.5 to 3.2.

<57>

The method of producing a purified chlorogenic acid-containing composition according to the above-mentioned item <55> or <56>, wherein the method of adjusting the pH is preferably a method involving adding an acid to the solution before treatment with the activated carbon or after treatment with the activated carbon, or a method involving bringing the solution before treatment with the activated carbon or after treatment with the activated carbon into contact with a cation exchange resin, more preferably a method involving bringing the solution before or after treatment with the activated carbon into contact with an H-type cation exchange resin.

<58>

The method of producing a purified chlorogenic acid-containing composition according to the above-mentioned item <57>, wherein the usage amount of the cation exchange resin is preferably from 0.1 mL/g to 10 mL/g, more preferably from 0.2 mL/g to 5 mL/g, even more preferably from 0.3 mL/g to 2 mL/g, with respect to the mass of the solids of the raw material chlorogenic acid-containing composition.

<59>

The method of producing a purified chlorogenic acid-containing composition according to the above-mentioned item <57> or <58>, wherein a method for the contact with the cation exchange resin is preferably a batchwise method or a continuous method, more preferably a continuous method involving continuously passing the solution through a column filled with the cation exchange resin.

<60>

The method of producing a purified chlorogenic acid-containing composition according to any one of the above-mentioned items <1> to <59>, preferably further comprising, after the third step, a step of subjecting the liquid having been treated with the activated carbon to one or two or more of solid-liquid separation selected from the group consisting of paper filtration, centrifugal separation, and membrane filtration.

<61>

The method of producing a purified chlorogenic acid-containing composition according to any one of the above-mentioned items <1> to <60>, wherein the purified chlorogenic acid-containing composition is preferably in a liquid, slurry, semisolid, or solid form.

<62>

The method of producing a purified chlorogenic acid-containing composition according to any one of the above-mentioned items <1> to <61>, wherein the purified chlorogenic acid-containing composition has a turbidity of preferably 200 NTU or less, more preferably 100 NTU or less, more preferably 40 NTU or less, even more preferably 20 NTU or less after production when the concentration of the chlorogenic acid is adjusted to 6 mass %.

<63>

The method of producing a purified chlorogenic acid-containing composition according to any one of the above-mentioned items <1> to <62>, wherein the purified chlorogenic acid-containing composition has a turbidity of preferably 500 NTU or less, more preferably 200 NTU or less, more preferably 100 NTU or less, more preferably 40 NTU or less, even more preferably 20 NTU or less after the concentration of the chlorogenic acid is adjusted to 6 mass % and the composition is stored at 5° C. for 12 hours.

<64>

The method of producing a purified chlorogenic acid-containing composition according to any one of the above-mentioned items <1> to <63>, wherein the content of the chlorogenic acid in the solids of the purified chlorogenic acid-containing composition is preferably from 10 mass % to 80 mass %, more preferably from 25 mass % to 75 mass %, even more preferably from 40 mass % to 70 mass %.

<65>

The method of producing a purified chlorogenic acid-containing composition according to any one of the above-mentioned items <1> to <64>, wherein the mass ratio (caffeine/chlorogenic acid) of caffeine to the chlorogenic acid in the purified chlorogenic acid-containing composition is preferably 0.01 or less, more preferably 0.005 or less, even more preferably 0.002 or less, or may be 0.

<66>

The method of producing a purified chlorogenic acid-containing composition according to any one of the above-mentioned items <1> to <65>, wherein the b value in the Lab color system of the purified chlorogenic acid-containing composition is preferably from 0 to 2.0, more preferably from 0 to 1.0, more preferably from 0 to 0.8, even more preferably from 0 to 0.5 when the concentration of the chlorogenic acid is adjusted to 0.064 mass %.

<67>

The method of producing a purified chlorogenic acid-containing composition according to any one of the above-mentioned items <1> to <66>, wherein the chlorogenic acid comprises preferably at least one selected from the group consisting of 3-caffeoylquinic acid, 4-caffeoylquinic acid, 5-caffeoylquinic acid, 3-feruloylquinic acid, 4-feruloylquinic acid, and 5-feruloylquinic acid, more preferably all of the above six.

EXAMPLES

1. Analysis of Chlorogenic Acid and Caffeine (Analyzer)

HPLC (manufactured by Hitachi, Ltd.) was used. The model numbers of component units in the analyzer are as follows:

Liquid feeding unit (with a built-in degasser): L-2130
Autosampler (with a cooler): L-2200
Column oven: L-2300
Separation column: Cadenza CD-C18, size: 4.6 mm i.d.× 150 mm, 3 µm (manufactured by Imtakt Corp.)
Detector (ultraviolet-visible absorption spectrophotometer): L-2420

(Analysis Conditions)

Sample injection volume: 10 µL
Flow rate: 1.0 mL/min
Ultraviolet absorption spectrophotometer detection wavelength: 325 nm (chlorogenic acid) and 270 nm (caffeine)
Eluent A: 5% acetonitrile containing 0.05 mol/L acetic acid, 0.01 mol/L sodium acetate, and 0.1 mmol/L 1-hydroxyethane-1,1-diphosphonic acid (HEDPO)
Eluent B: acetonitrile
Concentration Gradient Conditions (Vol %)

| Time | Eluent A | Eluent B |
|---|---|---|
| 0.0 min | 100% | 0% |
| 10.0 min | 100% | 0% |
| 15.0 min | 95% | 5% |
| 20.0 min | 95% | 5% |
| 22.0 min | 92% | 8% |
| 50.0 min | 92% | 8% |
| 52.0 min | 10% | 90% |
| 60.0 min | 10% | 90% |
| 60.1 min | 100% | 0% |
| 70.0 min | 100% | 0% |

(1) Retention Time of Chlorogenic Acid
3-Caffeoylquinic acid (3-CQA): 5.2 min
5-Caffeoylquinic acid (5-CQA): 8.7 min
4-Caffeoylquinic acid (4-CQA): 11.2 min
3-Feruloylquinic acid (3-FQA): 12.6 min
5-Feruloylquinic acid (5-FQA): 19.1 min
4-Feruloylquinic acid (4-FQA): 20.9 min
5-CQA was used as a standard substance to determine mass % based on the area % determined in the foregoing.

(2) Retention Time of Caffeine
Caffeine: 18.8 min
Reagent caffeine was used as a standard substance to determine mass % based on the area % determined in the foregoing.

2. Measurement of L Value

A sample was subjected to measurement with a colorimeter (manufactured by Nippon Denshoku Industries Co., Ltd., Spectrophotometer SE2000).

3. Analysis of Hue

Each of purified chlorogenic acid-containing compositions obtained in Examples and Comparative Examples was diluted with the eluent A (5% acetonitrile containing 0.05 mol/L acetic acid, 0.01 mol/L sodium acetate, and 0.1 mmol/L HEDPO) so that the concentration of chlorogenic acid was 0.064 mass %. After that, the sample was loaded into a quartz cell having an optical path length of 10 mm, and the b value in the Lab color system of the purified chlorogenic acid-containing composition after production was measured using a spectrophotometer (Spectro Color Meter ZE2000, manufactured by Nippon Denshoku Industries Co., Ltd.).

4. Analysis of Turbidity

Each of the purified chlorogenic acid-containing compositions obtained in Examples and Comparative Examples was diluted with ion-exchange water so that the concentration of chlorogenic acid was 6 mass %. After that, at 25° C., the turbidity (turbidity immediately after dilution to 6 mass %) of the purified chlorogenic acid-containing composition after production and the turbidity of the purified chlorogenic acid-containing composition after storage in a thermostatic chamber at 5° C. for 12 hours were measured using a turbidimeter (TN-100, manufactured by Eutech Instruments Pte Ltd.).

5. Analysis of Pore Volume and Specific Surface Area

The pore volume of activated carbon used in Examples and Comparative Examples and the specific surface area of acid clay used in Examples and Comparative Examples were measured by deaerating the activated carbon and acid clay sufficiently under vacuum at 120° C. or more and performing measurement using nitrogen gas at 77K with ASAP 2020 (manufactured by Micromeritics Instrument Corporation).

The activated carbon used in Examples is as shown in Table 1.

TABLE 1

| Abbreviation of activated carbon | Trade name | Sales company | Pore volume [mL/g] |
|---|---|---|---|
| SS | Granular Shirasagi WH2C SS | Japan EnviroChemicals Ltd. | 0.440 |
| GW | Kuraray Coal GW | Kuraray Coal | 0.484 |
| GWH | Kuraray Coal GWH | Kuraray Coal | 0.653 |
| LSS | WH2C LSS | Japan EnviroChemicals Ltd. | 0.951 |
| M20-SWC | M20-SWC | Calgon Mitsubishi Chemical Corporation | 1.10 |
| KL | Granular Shirasagi KL | Japan EnviroChemicals Ltd. | 1.22 |
| GLC | Kuraray Coal GLC | Kuraray Coal | 1.32 |
| SGP | Taiko SGP | Futamura Chemical Co., Ltd. | 1.51 |

Example 1

(Preparation of Raw Material Chlorogenic Acid-Containing Composition)

Robusta green coffee beans were subjected to extraction with hot water, and the resultant extract solution was dried by spray drying. Thus, a raw material chlorogenic acid-containing composition was obtained. The raw material chlorogenic acid-containing composition was found to contain 29.1 mass % of a chlorogenic acid and 8.8 mass % of caffeine and to have a mass ratio of caffeine/chlorogenic acid of 0.302.

(First Step)

394 g of the raw material chlorogenic acid-containing composition was mixed with 1,575 g of 60 mass % aqueous solution of ethanol, 197 g of acid clay (MIZUKA ACE #600, manufactured by Mizusawa Industrial Chemicals, Ltd., specific surface area: 95 m²/g), and 67 g of a filter aid (SOLKA FLOC, manufactured by Nippon Mining Procurement, Inc.), to obtain 2,233 g of a dispersion. The usage amount of the aqueous solution of organic solvent was 4 times by mass with respect to the solids of the raw material chlorogenic acid-containing composition. In addition, the usage amount of the acid clay was 50 parts by mass with respect to 100 parts by mass of the solids of the raw material chlorogenic acid-containing composition.

(Second Step)

Next, 2,233 g of the dispersion and 800 g of 60 mass % aqueous solution of ethanol were filtered through No. 2 filter paper with a precoat (a mixture of 25.5 g of diatom earth (Silica 100FA, manufactured by Chuo Silika Co., Ltd.) and 25.5 g of a filter aid (SOLKA FLOC, manufactured by Nippon Mining Procurement, Inc.)) deposited thereon, and 2,430 g of a filtrate was recovered. This solution is hereinafter referred to as "solution obtained in the second step". The "solution obtained in the second step" was found to contain 4.3 mass % of a chlorogenic acid and 0.86 mass % of caffeine and to have a mass ratio of caffeine/chlorogenic acid of 0.201, a pH of 5.8, and a b value of 3.06 when the solution was diluted so that the concentration of the chlorogenic acid was 0.064 mass %.

(Third Step)

Next, at 25° C., 259 g of the "solution obtained in the second step" and 157 g of an aqueous solution of organic solvent containing 60 mass % of ethanol were successively passed through a column filled with 105.6 mL (43.3 g) of activated carbon A (GWH, manufactured by Kuraray Coal), a column filled with 35.6 mL (8.5 g) of activated carbon B (GLC, manufactured by Kuraray Coal), and a column filled with 24.5 mL of an H-type cation exchange resin (SK1BH, manufactured by Mitsubishi Chemical Corporation) to recover a "column-treated solution". The usage amount of the activated carbon A was 1.45 times by mass with respect to the solids of the raw material chlorogenic acid-containing composition, and the usage amount of the activated carbon B was 0.29 time by mass with respect to the solids of the raw material chlorogenic acid-containing composition. The usage amount of the H-type cation exchange resin was 0.83 mL/g with respect to the mass of the solids of the raw material chlorogenic acid-containing composition.

Next, the "column-treated solution" was filtered through a filter with a pore size of 0.2 μm, and ethanol was distilled off using a rotary evaporator. Thus, 29.5 g of a "purified chlorogenic acid-containing composition" was obtained. The resultant purified chlorogenic acid composition was analyzed. The results are shown in Table 2.

Examples 2 to 4 and Comparative Examples 1 and 2

Purified chlorogenic acid compositions were obtained in the same manner as in Example 1 except that, in the third step, the activated carbon shown in Table 2 was used. The resultant purified chlorogenic acid compositions were analyzed. The results are shown in Table 2.

Example 5

In the same manner as in Example 1, a "solution obtained in the second step" was obtained. The "solution obtained in the second step" was found to contain 4.1 mass % of a chlorogenic acid and 0.81 mass % of caffeine and to have a mass ratio of caffeine/chlorogenic acid of 0.197, a pH of 6.0, and a b value of 3.11 when the solution was diluted so that the concentration of the chlorogenic acid was 0.064 mass %.

Next, at 25° C., 259 g of the "filtrate after solid-liquid separation" and 180 g of an aqueous solution of organic solvent containing 60 mass % of ethanol were successively passed through a column filled with 115.6 mL (45.1 g) of activated carbon A (LSS, manufactured by Japan Enviro Chemicals Ltd.), a column filled with 58.1 mL (8.7 g) of activated carbon B (SGP, manufactured by Futamura Chemical Co., Ltd.), and a column filled with 25.7 mL of an H-type cation exchange resin (SK1BH, manufactured by Mitsubishi Chemical Corporation) to recover a "column-treated solution". The usage amount of the activated carbon A was 1.56 times by mass with respect to the solids of the raw material chlorogenic acid-containing composition, and the usage amount of the activated carbon B was 0.31 time by mass with respect to the solids of the raw material chlorogenic acid-containing composition. The usage amount of the H-type cation exchange resin was 0.89 (mL/g) with respect to the mass of the solids of the raw material chlorogenic acid-containing composition.

Next, the "column-treated solution" was filtered through a filter with a pore size of 0.2 μm, and ethanol was distilled off using a rotary evaporator. Thus, 23.4 g of a "purified chlorogenic acid-containing composition" was obtained. The resultant purified chlorogenic acid composition was analyzed. The results are shown in Table 2.

Examples 6 to 8 and Comparative Examples 3 and 4

Purified chlorogenic acid compositions were obtained in the same manner as in Example 5 except that, in the third step, the activated carbon shown in Table 1 was used. The resultant purified chlorogenic acid compositions were analyzed. The results are shown in Table 2.

Example 9

A purified chlorogenic acid composition was obtained in the same manner as in Example 5 except that, in the third step, at 25° C., 259 g of the "solution obtained in the second step" and 177 g of the aqueous solution of organic solvent containing 60 mass % of ethanol were successively passed through a column filled with a mixture obtained by mixing 107.5 mL (45.2 g) of activated carbon A (GW, manufactured by Kuraray Chemical Co., Ltd.) and 58.1 mL (8.7 g) of activated carbon B (SGP, manufactured by Futamura Chemical Co., Ltd.) and a column filled with 25.7 mL of an H-type cation exchange resin (SK1BH, manufactured by Mitsubishi Chemical Corporation) to recover a "column-treated solution". The resultant purified chlorogenic acid composition was analyzed. The results are shown in Table 2.

Comparative Example 5

A purified chlorogenic acid composition was obtained in the same manner as in Example 5 except that, in the third step, at 25° C., 257 g of the "solution obtained in the second step" and 95 g of the aqueous solution of organic solvent containing 60 mass % of ethanol were successively passed through a column filled with 54.8 mL (8.2 g) of activated carbon (SGP, manufactured by Futamura Chemical Co., Ltd.) and a column filled with 24.3 mL of an H-type cation exchange resin (SK1BH, manufactured by Mitsubishi Chemical Corporation) to recover a "column-treated solution". The resultant purified chlorogenic acid composition was analyzed. The results are shown in Table 2.

TABLE 2

|  |  | Example | | | | | | | | | Comparative Example | | | | |
|---|---|---|---|---|---|---|---|---|---|---|---|---|---|---|---|
|  |  | 1 | 2 | 3 | 4 | 5 | 6 | 7 | 8 | 9 | 1 | 2 | 3 | 4 | 5 |
| First step | Concentration of organic solvent in aqueous solution of organic solvent used for dispersion or dissolution of raw material chlorogenic acid-containing preparation | 60% | 60% | 60% | 60% | 60% | 60% | 60% | 60% | 60% | 60% | 60% | 60% | 60% | 60% |
|  | Concentration of chlorogenic acid in raw material chlorogenic acid-containing preparation | 29% | 29% | 29% | 29% | 29% | 29% | 29% | 29% | 29% | 29% | 29% | 29% | 29% | 29% |
|  | Clay treatment | | | | | | | | | | | | | | |
| Second step | Method of removing precipitate | Treated Filtration | Treated Filtration | Treated Filtration | Treated Filtration | Treated Filtration | Treated Filtration | Treated Filtration | Treated Filtration | Treated Filtration | Treated Filtration | Treated Filtration | Treated Filtration | Treated Filtration | Treated Filtration |
|  | Concentration of organic solvent in solution obtained in second step | 60% | 60% | 60% | 60% | 60% | 60% | 60% | 60% | 60% | 60% | 60% | 60% | 60% | 60% |
|  | Concentration of chlorogenic acid in solution obtained in second step | 4.3% | 4.3% | 4.3% | 4.3% | 4.1% | 4.0% | 4.1% | 4.1% | 4.1% | 4.3% | 4.3% | 4.0% | 4.0% | 4.6% |
|  | pH (20° C.) of solution obtained in second step | 5.8 | 5.8 | 5.8 | 5.8 | 6 | 6 | 6 | 6 | 6 | 5.9 | 5.9 | 6 | 6 | 5.5 |
|  | b value of solution obtained in second step | 3.06 | 3.06 | 3.06 | 3.06 | 3.11 | 2.92 | 3.11 | 3.11 | 3.11 | 3.41 | 3.32 | 2.92 | 2.92 | 3.07 |
| Third step | Operation | Column | Column | Column | Column | Column | Column | Column | Column | Mixed column | Column | Column | Column | Column | — |
|  | Trade name of activated carbon | GWH | GW | SS | SS | LSS | GWH | GWH | SS | GW | GW | GW | M20-SWC | KL | — |
|  | Pore volume [mL/g] of activated carbon | 0.65 | 0.48 | 0.44 | 0.44 | 0.95 | 0.65 | 0.65 | 0.44 | 0.48 | 0.48 | 0.48 | 1.10 | 1.22 | — |
|  | Addition amount of activated carbon (with respect to mass of solids of raw material chlorogenic acid-containing composition) | 1.4 | 1.4 | 1.4 | 1.4 | 1.6 | 1.5 | 1.6 | 1.6 | 1.6 | 1.4 | 1.4 | 1.5 | 1.5 | — |

TABLE 2-continued

|  |  | Example | | | | | | | | | | Comparative Example | | | | |
|---|---|---|---|---|---|---|---|---|---|---|---|---|---|---|---|---|
|  |  | 1 | 2 | 3 | 4 | 5 | 6 | 7 | 8 | 9 | | 1 | 2 | 3 | 4 | 5 |
| Operation | | Column | Column | Column | Column | Column | Column | Column | Column | Mixed column | | Column | Column | Column | Column | Column |
| | Trade name of activated carbon | GLC | KL | KL | GLC | SGP | KL | SGP | SGP | SGP | | GW | SS | SGP | SGP | SGP |
| | Pore volume [mL/g] of activated carbon | 1.32 | 1.22 | 1.22 | 1.32 | 1.51 | 1.22 | 1.51 | 1.51 | 1.51 | | 0.48 | 0.44 | 1.51 | 1.51 | 1.51 |
| | Addition amount of activated carbon (with respect to mass of solids of raw material chlorogenic acid-containing composition) | 0.3 | 0.3 | 0.3 | 0.3 | 0.3 | 0.3 | 0.3 | 0.3 | 0.3 | | 0.3 | 0.3 | 0.3 | 0.3 | 0.3 |
| | Bed volume BV [L/L] with respect to total activated carbon | 1.97 | 1.77 | 1.86 | 2.14 | 1.62 | 1.66 | 1.66 | 1.78 | 1.69 | | 2.26 | 2.29 | 1.32 | 0.80 | 5.07 |
| | Superficial velocity SV [h⁻¹] with respect to total activated carbon | 0.30 | 0.26 | 0.28 | 0.32 | 0.24 | 0.25 | 0.25 | 0.27 | 0.25 | | 0.34 | 0.34 | 0.20 | 0.12 | 0.76 |
| | Addition amount [mL/g] of H-type cation exchange resin (with respect to mass of solids of raw material chlorogenic acid-containing composition) | 0.83 | 0.83 | 0.83 | 0.83 | 0.89 | 0.88 | 0.89 | 0.89 | 0.89 | | 0.79 | 0.80 | 0.88 | 0.88 | 0.73 |
| | Temperature of contact with activated carbon | 25° C. | 25° C. | 25° C. | 25° C. | 25° C. | 25° C. | 25° C. | 25° C. | 25° C. | | 25° C. | 25° C. | 25° C. | 25° C. | 25° C. |
| | Difference [(B) − (A)] [mL/g] between pore volumes of activated carbon | 0.67 | 0.74 | 0.78 | 0.88 | 0.56 | 0.57 | 0.86 | 1.07 | 1.03 | | 0.00 | 0.04 | 0.41 | 0.29 | — |
| | Ratio [(B)/(A)] of pore volumes of activated carbon | 2.02 | 2.52 | 2.77 | 3.00 | 1.59 | 1.87 | 2.31 | 3.43 | 3.12 | | 1.00 | 0.91 | 1.37 | 1.24 | — |
| | Mass ratio [(B)/(A)] of addition amounts of activated carbon | 0.20 | 0.20 | 0.20 | 0.20 | 0.20 | 0.20 | 0.20 | 0.20 | 0.20 | | 0.20 | 0.20 | 0.20 | 0.20 | 8 |
| Analysis | Concentration of chlorogenic acid in solids of purified chlorogenic acid-containing composition | 40% | 51% | 53% | 49% | 34% | 43% | 50% | 60% | 60% | | 49% | 55% | 6% | 15% | 53% |
| | b value of purified chlorogenic | 0.76 | 0.46 | 0.42 | 0.83 | 0.87 | 0.28 | 0.42 | 0.44 | 0.59 | | 2.91 | 2.58 | 4.79 | 0.90 | 0.40 |

TABLE 2-continued

| | Example | | | | | | | | | Comparative Example | | | | |
|---|---|---|---|---|---|---|---|---|---|---|---|---|---|---|
| | 1 | 2 | 3 | 4 | 5 | 6 | 7 | 8 | 9 | 1 | 2 | 3 | 4 | 5 |
| acid-containing composition pH of purified chlorogenic acid-containing composition | 1.1 | 1.3 | 1.8 | 2.1 | 0.6 | 0.8 | 0.8 | 1.7 | 0.8 | 2.1 | 2.5 | 0.8 | 1.0 | 2.8 |
| Δb value (b value of "solution obtained in second step" − b value of "purified chlorogenic acid-containing composition" | 2.30 | 2.60 | 2.64 | 2.23 | 2.24 | 2.64 | 2.69 | 2.67 | 2.52 | 0.50 | 0.74 | −1.86 | 2.03 | 2.67 |
| Yield of chlorogenic acid | 37% | 65% | 69% | 66% | 28% | 37% | 46% | 72% | 63% | 72% | 76% | 3% | 4% | 87% |
| Loss of chlorogenic acid | 63% | 35% | 31% | 34% | 72% | 63% | 54% | 28% | 37% | 28% | 24% | 97% | 96% | 13% |
| Δb value/loss (%) of chlorogenic acid × 100 | 4.8 | 8.8 | 8.5 | 8.9 | 3.1 | 4.2 | 5.0 | 9.4 | 6.8 | 1.8 | 3.1 | −1.9 | 2.1 | 21.3 |
| Turbidity (25° C.) [NTU] | 2 | 8 | 6 | 3 | 3 | 8 | 3 | 4 | 2 | over range Precipitated | over range Precipitated | 5 | 89 | 1,000 |
| Turbidity (5° C.) [NTU] | 2 | 4 | 6 | 1 | 3 | 2 | 3 | 3 | 3 | Precipitated | Precipitated | — | — | Precipitated |
| Mass ratio of caffeine/chlorogenic acid | 0.0010 | 0.0014 | 0.0012 | 0.0014 | 0.0013 | 0.0007 | 0.0011 | 0.0010 | 0.0006 | 0.0011 | 0.0010 | 0.0015 | 0.0008 | 0.1085 |

Example 10

In the same manner as in Example 1, a "solution obtained in the second step" was obtained. The "solution obtained in the second step" was found to contain 4.5 mass % of a chlorogenic acid and 0.92 mass % of caffeine and to have a mass ratio of caffeine/chlorogenic acid of 0.204, a pH of 6.0, and a b value of 3.50 when the solution was diluted so that the concentration of the chlorogenic acid was 0.064 mass %.

Next, at 25° C., 257 g of the "solution obtained in the second step" and 178 g of an aqueous solution of organic solvent containing 60 mass % of ethanol were successively passed through a column filled with 101.4 mL (42.6 g) of activated carbon (GW, manufactured by Kuraray Coal), a column filled with 54.8 mL (8.2 g) of activated carbon B (SGP, manufactured by Futamura Chemical Co., Ltd.), and a column filled with 24.3 mL of an H-type cation exchange resin (SK1BH, manufactured by Mitsubishi Chemical Corporation) to recover a "column-treated solution". The usage amount of the activated carbon A was 1.31 times by mass with respect to the solids of the raw material chlorogenic acid-containing composition, and the usage amount of the activated carbon B was 0.26 time by mass with respect to the solids of the raw material chlorogenic acid-containing composition. The usage amount of the H-type cation exchange resin was 0.75 (mL/g) with respect to the mass of the solids of the raw material chlorogenic acid-containing composition.

Next, the "column-treated solution" was filtered through a filter with a pore size of 0.2 μm, and ethanol was distilled off using a rotary evaporator. Thus, 42.5 g of a "purified chlorogenic acid-containing composition" was obtained. The resultant purified chlorogenic acid composition was analyzed. The results are shown in Table 3.

Examples 11 to 15

Purified chlorogenic acid compositions were obtained in the same manner as in Example 10 except that, in the third step, the kind and addition amount of the activated carbon shown in Table 3 were used. The resultant purified chlorogenic acid compositions were analyzed. The results are shown in Table 3.

TABLE 3

|  |  | Example | | | | | |
|---|---|---|---|---|---|---|---|
|  |  | 10 | 11 | 12 | 13 | 14 | 15 |
| First step | Concentration of organic solvent in aqueous solution of organic solvent used for dispersion or dissolution of raw material chlorogenic acid-containing preparation | 60% | 60% | 60% | 60% | 60% | 60% |
|  | Concentration of chlorogenic acid in raw material chlorogenic acid-containing preparation | 29% | 29% | 29% | 29% | 29% | 29% |
|  | Clay treatment | Treated | Treated | Treated | Treated | Treated | Treated |
| Second step | Method of removing precipitate | Filtration | Filtration | Filtration | Filtration | Filtration | Filtration |
|  | Concentration of organic solvent in solution obtained in second step | 60% | 60% | 60% | 60% | 60% | 60% |
|  | Concentration of chlorogenic acid in solution obtained in second step | 4.4% | 4.3% | 4.3% | 4.3% | 4.4% | 4.6% |
|  | pH (20° C.) of solution obtained in second step | 6.0 | 5.9 | 5.9 | 5.9 | 6.0 | 5.5 |
|  | b value of solution obtained in second step | 3.50 | 3.52 | 3.32 | 3.32 | 3.50 | 3.07 |
| Third step | Operation | Column | Column | Column | Column | Column | Column |
|  | Trade name of activated carbon | GW | GW | GW | SGP | GW | GW |
|  | Pore volume [mL/g] of activated carbon | 0.48 | 0.48 | 0.48 | 1.51 | 0.48 | 0.48 |
|  | Addition amount of activated carbon (with respect to mass of solids of raw material chlorogenic acid-containing composition) | 1.3 | 1.0 | 0.7 | 0.3 | 1.3 | 0.3 |
|  | Operation | Column | Column | Column | Column | Column | Column |
|  | Trade name of activated carbon | SGP | SGP | SGP | GW | GLC | SGP |
|  | Pore volume [mL/g] of activated carbon | 1.51 | 1.51 | 1.51 | 0.48 | 1.32 | 1.51 |
|  | Addition amount of activated carbon (with respect to mass of solids of raw material chlorogenic acid-containing composition) | 0.3 | 0.3 | 0.3 | 0.7 | 0.3 | 0.3 |
|  | Bed volume BV [L/L] with respect to total activated carbon | 1.78 | 2.09 | 2.6 | 2.6 | 2.04 | 3.47 |
|  | Superficial velocity SV [$h^{-1}$] with respect to total activated carbon | 0.27 | 0.31 | 0.39 | 0.39 | 0.31 | 0.52 |
|  | Addition amount [mL/g] of H-type cation exchange resin (with respect to mass of solids of raw material chlorogenic acid-containing composition) | 0.75 | 0.8 | 0.79 | 0.80 | 0.75 | 0.73 |
|  | Temperature of contact with activated carbon | 25° C. | 25° C. | 25° C. | 25° C. | 25° C. | 25° C. |
| Analysis | Difference [(B) − (A)] [mL/g] between pore volumes of activated carbon | 1.03 | 1.03 | 1.03 | 1.03 | 0.84 | 1.03 |
|  | Ratio [(B)/(A)] of pore volumes of activated carbon | 3.12 | 3.12 | 3.12 | 0.32 | 2.72 | 3.12 |
|  | Mass ratio [(B)/(A)] of addition amounts of activated carbon | 0.20 | 0.27 | 0.40 | 2.50 | 0.20 | 0.80 |
|  | Concentration of chlorogenic acid in solids of purified chlorogenic acid-containing composition | 54% | 56% | 56% | 55% | 51% | 55% |
|  | b value of purified chlorogenic acid-containing composition | 0.47 | 0.35 | 0.38 | 0.90 | 0.88 | 0.30 |
|  | pH of purified chlorogenic acid-containing composition | 2.4 | 1.9 | 2.1 | 2.4 | 2.2 | 2.6 |
|  | Δb value (b value of "solution obtained in second step" − b value of "purified chlorogenic acid-containing composition" | 3.03 | 3.17 | 2.94 | 2.42 | 2.62 | 2.77 |
|  | Yield of chlorogenic acid | 70% | 76% | 78% | 74% | 66% | 79% |
|  | Loss of chlorogenic acid | 30% | 24% | 22% | 26% | 34% | 21% |
|  | Δb value/loss (%) of chlorogenic acid × 100 | 10.3 | 13.2 | 13.3 | 9.3 | 7.7 | 13.5 |
|  | Turbidity (25° C.) [NTU] | 7 | 3 | 12 | 46 | 8 | 14 |
|  | Turbidity (5° C.) [NTU] | 5 | 4 | 15 | Precipitated | 2 | 465 |
|  | Mass ratio of caffeine/chlorogenic acid | 0.0007 | 0.0005 | 0.0004 | 0.0011 | 0.0011 | 0.0076 |

As is apparent from Table 2 and Table 3, it found that a purified chlorogenic acid-containing composition having a good hue even when the concentration of a chlorogenic acid is diluted to an optimum concentration as a drink to provide an acidic drink, having a reduced turbidity after production, and having a reduced caffeine content can be produced without reducing the content of the chlorogenic acid by performing a method involving, as essential steps, the first step to the third step according to the invention of the present application in which specific activated carbon having controlled pore volumes is used in the third step.

The invention claimed is:

1. A method of producing a purified chlorogenic acid-containing composition, comprising:
    a first step of adding together a raw material chlorogenic acid-containing composition and an aqueous solution of organic solvent to form a dispersion or solution;
    a second step of removing a precipitate from the dispersion or the solution obtained in the first step to form a solution; and
    a third step of bringing the solution obtained in the second step into contact with activated carbon comprising activated carbon (A) having a pore volume of from 0.3 mL/g to 1.0 mL/g and activated carbon (B) having a pore volume larger than that of the activated carbon (A) to form said purified chlorogenic acid-containing composition,
    wherein a difference [(B)−(A)] in pore volume between the activated carbon (A) and the activated carbon (B) is from 0.1 mL/g to 1.5 mL/g.

2. The method of producing a purified chlorogenic acid-containing composition according to claim 1, wherein the difference [(B)−(A)] in pore volume between the activated carbon (A) and the activated carbon (B) is from 0.5 mL/g to 1.5 mL/g.

3. The method of producing a purified chlorogenic acid-containing composition according to claim 1, wherein a ratio of the pore volume of the activated carbon (B) to the pore volume of the activated carbon (A), [(B)/(A)], is from 1.5 to 4.0.

4. The method of producing a purified chlorogenic acid-containing composition according to claim 1, wherein a mass ratio of the activated carbon (B) to the activated carbon (A), [(B)/(A)], is from 0.1 to 1.0.

5. The method of producing a purified chlorogenic acid-containing composition according to claim 1, wherein a mass ratio of the activated carbon (B) to the activated carbon (A), [(B)/(A)], is from 0.1 to 0.7.

6. The method of producing a purified chlorogenic acid-containing composition according to claim 1, wherein the activated carbon (A) has a pore volume of from 0.33 mL/g to 0.94 mL/g.

7. The method of producing a purified chlorogenic acid-containing composition according to claim 1, wherein the activated carbon (A) has a pore volume of from 0.37 mL/g to 0.64 mL/g.

8. The method of producing a purified chlorogenic acid-containing composition according to claim 1, wherein the activated carbon (B) has a pore volume of from 1.0 mL/g to 2.0 mL/g.

9. The method of producing a purified chlorogenic acid-containing composition according to claim 1, wherein in the third step, the solution obtained in the second step is brought into contact with the activated carbon (A) and the activated carbon (B) separately.

10. The method of producing a purified chlorogenic acid-containing composition according to claim 1, wherein in the third step, the solution obtained in the second step is brought into contact with the activated carbon (A) and then with the activated carbon (B).

11. The method of producing a purified chlorogenic acid-containing composition according to claim 1, wherein a concentration of an organic solvent in the aqueous solution of organic solvent is from 10 mass % to 95 mass %.

12. The method of producing a purified chlorogenic acid-containing composition according to claim 1, wherein an organic solvent in the aqueous solution of organic solvent is ethanol.

13. The method of producing a purified chlorogenic acid-containing composition according to claim 1, wherein in the first step, one or more selected from the group consisting of acid clay, activated clay, and a filter aid is added to said dispersion or solution.

14. The method of producing a purified chlorogenic acid-containing composition according to claim 1, further comprising, after the second step and before the third step, or after the third step, adjusting a pH of the solution before treatment with the activated carbon or after treatment with the activated carbon to from 0.2 to 3.8.

15. The method of producing a purified chlorogenic acid-containing composition according to claim 1, wherein an amount of the activated carbon (A) in the third step is from 0.4 time by mass to 2.0 times by mass with respect to solids in the raw material chlorogenic acid-containing composition in the first step.

16. The method of producing a purified chlorogenic acid-containing composition according to claim 1, wherein an amount of the activated carbon (B) in the third step is from 0.1 time by mass to 0.8 time by mass with respect to solids in the raw material chlorogenic acid-containing composition in the first step.

* * * * *